United States Patent
Lin et al.

(10) Patent No.: US 7,201,921 B2
(45) Date of Patent: *Apr. 10, 2007

(54) ANTIHISTAMINE FORMULATIONS FOR SOFT CAPSULE DOSAGE FORMS

(75) Inventors: Jing Lin, Mulgrave (AU); Hung Truong, Chadstone (AU)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 534 days.

This patent is subject to a terminal disclaimer.

(21) Appl. No.: 10/384,868

(22) Filed: Mar. 10, 2003

(65) Prior Publication Data

US 2003/0215495 A1    Nov. 20, 2003

Related U.S. Application Data

(63) Continuation-in-part of application No. 09/909,313, filed on Jul. 20, 2001, now Pat. No. 6,720,002.

(51) Int. Cl.
*A61K 9/66* (2006.01)
*A61K 9/48* (2006.01)

(52) U.S. Cl. ............ 424/455; 424/452; 424/456; 424/462

(58) Field of Classification Search ............ 424/455, 424/452, 450, 451, 462, 456
See application file for complete search history.

(56) References Cited

U.S. PATENT DOCUMENTS

| | | |
|---|---|---|
| 6,248,363 B1 * | 6/2001 | Patel et al. .......... 424/497 |
| 2001/0036472 A1 * | 11/2001 | Wong et al. .......... 424/456 |
| 2002/0012675 A1 * | 1/2002 | Jain et al. .......... 424/400 |
| 2003/0104048 A1 * | 6/2003 | Patel et al. .......... 424/451 |
| 2003/0108607 A1 * | 6/2003 | Szymczak .......... 424/479 |

* cited by examiner

*Primary Examiner*—Sharon E. Kennedy
(74) *Attorney, Agent, or Firm*—Donald O. Nickey; Andrew G. Rozycki

(57) ABSTRACT

The invention herein relates to a pharmaceutical composition containing loratadine and derivatives thereof which is suitable for use in soft capsule dosage forms. A pharmaceutical composition according to the invention comprises loratadine and derivatives thereof in a pharmaceutically effective amount; and a solvent system comprising a mixture of medium chain fatty acids. The loratadine compositions exhibit good solubility and storage stability while maintaining bioavailability of the drug. The compositions also permit high concentrations of solubilized loratadine per total fill volume and thereby permit the use of smaller capsules to deliver the same dosage of drug.

7 Claims, No Drawings

ANTIHISTAMINE FORMULATIONS FOR SOFT CAPSULE DOSAGE FORMS

RELATED APPLICATION DATA

This application is a continuation-in-part (CIP) of U.S. patent application Ser. No. 09/909,313 filed Jul. 20, 2001, now U.S. Pat. No. 6,720,002 issued Apr. 13, 2004.

FIELD OF THE INVENTION

The invention relates to the field of pharmaceutical compositions. In particular, the invention pertains to pharmaceutical formulations containing antihistamines, such as, loratadine and its derivatives that are formulated for use in conjunction with soft capsules.

BACKGROUND OF THE INVENTION

Two identified histamine receptors are the receptors H-1 and H-2. The H-1 receptors mediate the response antagonized by conventional antihistamines. H-1 receptors are present in the mammalian skin, ileum and bronchial smooth muscle.

Non-narcotic or non-sedating hydrophobic antihistamine compounds such as loratadine and its derivatives are known. Loratadine was first described in U.S. Pat. No. 4,282,233 to Vilani. Loratadine is an H-1 histamine receptor protein antagonist which binds to peripheral H-1 receptors as discussed in Quercia et al., Hosp. Formul., 28, p. 137–53 (1993). Loratadine is useful as an antihistamine and has little or no sedative effects. Thus, loratadine provides an antihistamine effect while still allowing the user to perform mental or physical functions requiring high levels of concentration. A variety of other therapeutic treatments using loratadine alone or in combination with other active ingredients have been suggested, such as treatment of seasonal or perennial rhinitis, allergic asthma, and motion sickness. See Aberg et al., U.S. Pat. No. 5,731,319, for example. Antiarrhythmic uses, such as treatment of atrial fibrillation (AF), have also been suggested, as described in Buckland et al., U.S. Pat. No. 6,110,927.

Loratadine derivatives which share antihistamine properties of loratadine have also been developed. Active metabolites such as decarbalkoxylated forms of loratadine have been of interest. One such metabolite derivative is 8-chloro-6,11-dihydro-11-(4-piperidylidine)-5H-benzo-[5,6]-cyclohepta-[1,2-b] pyridine, also known as descarboethoxyloratadine (DCL) which is described in U.S. Pat. No. 4,659,716. U.S. Pat. No. 5,595,997 to Aberg et al discloses methods of utilizing DCL for the treatment of allergic rhinitis and other disorders without adverse side effects.

Other patents relating to loratadine or a chemically related antihistamine, including any pharmaceutically acceptable salt thereof, in various dosage forms include U.S. Pat. No. 5,100,675 to Cho et al.; U.S. Pat. No. 4,990,535 to Cho et al.; and U.S. Pat. No. 5,314,697 to Kwan et al.

Oral dosage forms, such as loratadine-containing tablets and syrups, are known and marketed under the names Claritin®, Claratin Reditabs® and Claratin-D® 24-Hour etc. (commercially available from Schering-Plough Corporation, NJ).

These commercial products are described in U.S. Pat. No. 4,282,233 to Villani; U.S. Pat. No. 4,659,716 to Villani; U.S. Pat. No. 4,863,931 to Schumacher et al.; U.S. Pat. No. 6,132,758 to Munayyer et al. U.S. Pat. No. 6,132,758 discloses an antihistaminic syrup stabilized against degradation of the active ingredient by the addition of about 0.05 to 5 mg/mL of an amino-polycarboxylic acid. This patent teaches that under certain storage conditions losses of active agent can occur.

U.S. Pat. No. 4,910,205 to Kogan et al discloses a transdermally acceptable composition comprising an effective amount of loratadine or its decarbalkoxylation product, about 40–70% weight % of a volatile solvent, about 5–50% by weight of a fatty acid ester and about 2–60% of an essential oil.

While syrup, solid and fast dissolving dosage forms are available for loratadine type antihistamines, there presently exists a need for a soft capsule dosage form. The soft capsule dosage form has many advantages known to those skilled in the art, however, formulating hydrophobic drugs into solutions for encapsulation into a soft capsule can present many problems. Oral delivery systems for hydrophobic drugs are known. Lacy et al. U.S. Pat. No. 6,096,338 describes delivery systems for hydrophobic drugs including histamine H-1 receptor antagonists such as loratadine. The carrier systems disclosed include a digestible oil, preferably mixtures of partial or complete esters of medium chain fatty acids, and a pharmaceutically acceptable surfactant component comprising a hydrophilic surfactant containing a transesterification product of polyoxyethylene glycol with glycerol esters of capric and/or caprylic acids. This surfactant disperses the oil in vivo without substantially inhibiting in vivo lipolysis of the oil. The reference does not, however, specifically address the problems associated with storage stability and recrystallization of loratadine and its derivatives in soft capsule dosage forms.

Hydrophobic solvents are preferred for use in soft capsules so as to reduce the hydrophilic nature of the fill, wherein migration of water through the soft capsular material into the fill composition can cause recrystallization and precipitation of the active ingredient under storage conditions. One problem associated with hydrophobic solvents, however, is that they are known to adversely affect bioavailability of the drug. Compounds such as loratadine are susceptible to recrystallization and therefore experience the solvent system challenges associated with soft capsules. Ideally, a solvent system for loratadine and its derivatives is one which is hydrophobic, protonic and water-dispersible.

There thus exists a need for improved pharmaceutical formulations containing loratadine and derivatives thereof for use in soft capsules which solubilize loratadine and exhibit long-term storage stability at ambient conditions without recrystallization. There is also a need for a solvent system which does not adversely affect bioavailability of the active ingredient. Even more desirable would be a formulation which satisfies both of these criteria and also increase the fill concentration of loratadine. This would permit the use of smaller size capsules for a given dose of active.

SUMMARY OF THE INVENTION

The invention provides for a pharmaceutical composition comprising loratadine and its derivatives together with a solvent system for use in soft capsules. Loratadine compositions of the invention exhibit unexpected and improved solubilization properties at ambient storage conditions over extended period of time without recrystallization and precipitation of loratadine. The inventive composition also permits higher concentrations of loratadine to be delivered within a given fill volume. As a result, the total amount of fill volume needed to administer the same dosage of loratadine is reduced, and smaller capsule sizes can be used thereby improving patient comfort and reducing manufacturing costs.

The invention provides a pharmaceutical composition for use in soft capsules comprising loratadine and derivatives thereof and a solvent system comprising a mixture of mono- and diglycerides of medium chain fatty acids. In a more preferred embodiment the invention provides a pharmaceutical composition that additionally comprises a dispersant. In a most preferred embodiment the dispersant comprises povidone and polyoxyethylene sorbitan fatty acid ester (e.g., Polysorbate™ 80).

There is further disclosed a pharmaceutical composition for use in soft capsule dosage form consisting essentially of:
  a) loratadine and derivatives thereof present in an amount of about 6.3% by weight of the total composition;
  b) mono- and di-glycerides of medium chain fatty acids present in an amount of about 87% by weight of the total composition;
  c) povidone present in an amount of about 6.3% by weight of the total composition; and
  d) polyoxyethylene sorbitan fatty acid ester present in an amount of about 0.8% by weight of the total composition.

There is also disclosed a pharmaceutical composition for use in soft capsule dosage forms consisting essentially of:
  a) decarbalkoxylated loratadine derivative in a pharmaceutically effective amount;
  b) mono- and di-glycerides of medium chain fatty acids comprising caprylic acid and capric acid;
  c) povidone; and
  d) polyoxyethylene sorbitan fatty acid ester.

There is further disclosed a soft capsule dosage form comprising a fill composition consisting essentially of:
  a) loratadine and derivatives thereof in a pharmaceutically effective amount;
  b) a mixture of mono- and diglycerides of medium chain fatty acids;
  c) povidone;
  d) polyoxyethylene sorbitan fatty acid ester; and
  wherein said soft capsule has a capsule size of 5 minim or less.

Loratadine is the drug name given to the compound known as ethyl 4-(8-chloro-5,6-dihydro-11H-benzo[5,6]cyclohepta[1,2-b]pyridin-11-ylidene)-1-piperidinecarboxylate. A structure for this compound is:

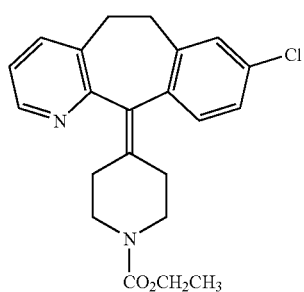

(I)

Loratadine derivatives include compounds having the structural formula of loratadine and having substituents differing from that of loratadine and having substantially the same chemical and therapeutic properties. Loratadine derivatives include, but are not limited to, decarboalkoxylated forms of loratadine, such as 8-chloro-6,11-dihydro-1-(4-piperidylidine)-5H-benzo-[5,6]-cyclohepta-[1,2-b] pyridine, also known as descarboethoxyloratadine (DCL); and azatadine. As used herein and in the claims the phrase "loratadine and derivatives thereof" means loratadine or any chemically related antihistamine, including any pharmaceutically acceptable salt thereof. Chemically reacted antihistamines include any halogenated H-benzo-cyclohepta-pyridine.

Loratadine and derivatives thereof can be present in an amount of about 6.3% or less by weight of the total fill composition. Typically, loratadine and derivatives thereof can be present in an amount of about 6.3% to about 3.0% by weight of the total fill composition.

Solvent systems which can be used in accordance with the invention are those which are both moderately lipophilic and have hydrogen bonding capability. Preferably, the solvent system has a hydrophilic lipophilic balance (HLB) value ranging from about 3 to about 7, more preferably ranging from about 4 to about 5. The preferred solvent system of the invention contains a mixture of mono- and diglycerides of medium chain fatty acids. Preferred mixtures of mono- and diglycerides of medium chain fatty acids comprise mixtures of caprylic and capric acid. Most preferred as the mixture of mono- and diglyceride medium chain fatty acids is CAPMUL™ MCM-C8 (available from Abitec Corporation, Northampton, England). The mono- and diglyceride mixture can be present in an amount of about 89.0% by weight or less of the total fill composition. When CAPMUL™ MCM-C8 is used, it is preferably present in an amount ranging from about 89.0% to about 70.0%, more preferably about 89.0% to about 80%, by weight of the total fill composition.

The solvent system can further comprise a dispersant composition to enhance uniform dispersibility of the fill in water or gastric juices. The amount of the additional dispersant, however, is present in amount sufficient to enhance uniform dispersion of the fill in water or gastric juices without significantly increasing the volume of the fill. When a dispersant is used, it is preferred that the dispersant be present in an amount of 8.0% by weight of the fill or less. More preferred is a dispersant present in an amount of from about 7.5% to about 5.0%, most preferably from about 7.5% to about 7.0%, by weight of the total fill composition.

A preferred dispersant is a mixture of povidone (polyvinylpyrrolidone) and polyoxyethylene sorbitan fatty acid ester. Suitable polyoxyethylene sorbitan fatty acid esters which can be used include, but are not limited to, Polysorbate™ 80. Mixtures of povidone and Polysorbate™ 80 can preferably be present in a weight ratio of about 10:1 to about 15:1, respectively. Other polyoxyethylene sorbitan fatty acid esters which can be used include Polysorbate™ 40, Polysorbate™ 60, Polysorbate™ 20 and Polysorbate™ 120.

Compositions according to the invention do not require the presence of additional ingredients such as additives and stabilizers typically associated with soft capsule fill formulations. Without these additional ingredients higher concentrations of loratadine and derivatives thereof can be obtained within smaller fill volumes as compared to existing formulations.

The invention further provides a soft dosage form having a pharmaceutical composition comprising loratadine and derivatives thereof and a solvent system having a mixture of medium chain mono- and diglycerides. In one embodiment, the invention includes a soft capsule comprising a storage stable composition having 10 mg of loratadine in solubilized state in a capsule size as small as 3 minims.

DETAILED DESCRIPTION OF THE INVENTION

The loratadine compounds of the invention can be prepared according to the method described in Villani U.S. Pat. No. 4,282,233, the entire text of which is incorporated herein by reference. The starting materials and reagents to prepare loratadine and its derivatives are well known in the art and readily available, and loratadine and its derivatives can be synthesized using conventional organic synthesis techniques. Metabolic derivatives of loratadine, such as decarbalkoxylated forms of loratadine, can be prepared by removal of the carbethoxy moiety according to methods known in the art and as described in U.S. Pat. No. 4,659,716, the entire text of which is incorporated herein by reference. For example, loratadine can be refluxed in the presence of sodium hydroxide and ethanol to remove the carbethoxy moiety from the piperidine ring of the compound structure.

Solvent systems which can be used in accordance with the invention are those which are both moderately lipophilic and have hydrogen bonding capability. Preferably, the solvent system has a hydrophilic lipophilic balance (HLB) value ranging from about 3 to about 7, more preferably ranging from about 4 to about 5. Suitable solvent systems include, but are not limited to, polyglycolized glycerides (such as LABRAFIL® WL 2609BS available from Gattefosse, Binfield, U.K.), propylene glycol monolaurate (such as LAUROGLYCOL™ 90 available from Gattefosse), propylene glycol monocaprylate (such as CAPRYOL™ 90 available from Gattefosse), and mono- and diglyceride medium chain fatty acids. Most preferred is the mono-, diglyceride medium chain fatty acid mixture CAPMUL™ MCM C8 (commercially available from Abitec Corporation).

The solvent system can further comprise a dispersant composition to enhance uniform dispersibility of the fill in water. The amount of the additional dispersant, however, is present in amount sufficient to enhance uniform dispersion of the fill in water or gastric juices without significantly increasing the volume of the fill. When a dispersant is used, it is preferred that the dispersant be present in an amount of 8.0% by weight of the fill or less. Most preferred is a dispersant present in an amount of from about 7.5% to about 7.0% by weight of the total fill composition.

The dispersant composition used in accordance with the invention can be a combination of povidone together with a surfactant. Suitable surfactants which can be used include, but are not limited to, non-ionic surfactants having an HLB value ranging from about 14 to about 17; polyoxyethylene sorbitan fatty acid esters, such as Polysorbate™ 40, Polysorbate™ 80, Polysorbate™ 60, Polysorbate™ 20, and Polysorbate™ 120; ethoxylated aliphatic alcohols, such as Oleth-20 (Volpo™ 20 available from Croda, Inc., Parsippany, N.J.), Ceteareth-20 (Volpo™ CS-20 available from Croda, Parsippany, N.J.); and caprylocaproyl macrogol-8 glycerides (LAUROGLYCOL™ 90 available from Gattefosse).

A preferred dispersant is a mixture of povidone and Polysorbate™ 80. Mixtures of povidone (polyvinyl pyrrolidone) and Polysorbate™ 80 (polyoxyethylene sorbitan fatty acid monooleate) can be present in a ratio of about 10:1 to about 15:1.0, respectively.

Soft capsules containing pharmaceutical compositions can be prepared using conventional and known encapsulation techniques, such as that described in Stroud et al., U.S. Pat. No. 5,735,105, the entire text of which is incorporated herein by reference. In general, the formulation is deposited between two opposing ribbons of a gel composition. The composition of the ribbons may include gelatin, modified starches, gums, carrageenans and mixtures thereof.

Carrageenans are water-soluble gums comprising linear polysaccharides with a sugar backbone of alternating units consisting of galactose units linked by 1,3-β-D-linkages, as well as 1,4-α-D-linkages. The fundamental properties of iota, kappa and lambda are a function of the number and position of the ester sulfate groups. Preferred carrageenan capsule materials are those comprising iota-carrageenan. Iota-carrageenan contains approximately 30% by weight 3,6 anhydro-D-galactose and 32% ester sulfate by weight. Particularly preferred are iota-carrageenan materials described in Tanner et al., U.S. Pat. No. 6,340,473, the entire text of which is incorporated herein by reference, which comprises iota-carrageenan, modified starch, plasticizer and a dibasic buffer system. Carrageenan-containing capsule materials are available under the tradename VEGICAPS™ and available from Cardinal Health, Inc., Somerset, N.J.).

Modified starches that can be used in accordance with the invention include hydroxypropylated starches, acid thinned starches and the like. The only native starch determined to be functional with iota-carrageenan in preparing the capsular material films of the invention is potato starch, and the term "modified starch" is meant to include native, unmodified potato starch. In general, modified starches are products prepared by chemical treatment of starches, for example, acid treatment starches, enzyme treatment starches, oxidized starches, cross-bonding starches, and other starch derivatives. It is preferred that the modified starches be derivatized wherein side chains are modified with hydrophilic or hydrophobic groups to thereby form more complicated structure with a strong interaction between side chains.

Suitable plasticizers include the materials used for the same purpose in the manufacture of mammalian gelatin capsules. Representative plasticizers are any of a variety of polyhydric alcohols such as glycerin, sorbitol, propylene glycol, polyethylene glycol and the like. Other plasticizers can include saccharides and polysaccharides, which can be prepared by hydrolysis and/or hydrogenation of simple or complex polysaccharides.

Other components can also be incorporated into the carrageenan capsule compositions provided they do not alter the melting point/fusion point characteristics of the film. Representative of these additional components, typically added during the molten state of the capsule composition, include flavoring agents, opacifying agents, preservatives, embrittlement inhibiting agents, colorants, dyes and pigments, and disintegrants. Use of conventional pharmaceutical or food grade ingredients are acceptable.

Those skilled in the art will appreciate what capsule material compositions are suitable. The opposing ribbons are then run between two die rollers having die pockets thereon the surface of which corresponds to the configuration of the desired soft capsule. The composition is sealed within the fused casing.

When formulated in accordance with the invention, a 10 mg loratadine dose can be accommodated by a 5 minim or less size oval soft capsule. A 10 mg loratadine dose can be contained within a capsule size as small as a 3 minim size oval soft capsule. Capsule size volumes of the invention are herein expressed in terms of minims. A minim is a pharmaceutical volumetric unit of measure wherein 1 minim=0.0616 cc.

Soft capsule forms, such as soft gelatin or Vegicaps™ soft capsules, containing the loratadine compositions of the invention can be orally administered to patients in need of H1 receptor antagonist or antihistamine treatment.

The invention can be further illustrated by the following Examples:

EXAMPLE 1

Process of Preparing Loratadine Formulation

CAPMUL™ MCM C8, povidone, and Polysorbate™ 80 were combined. The mixture was heated to about 60° C. until the povidone was completely dissolved. Loratadine was added to the mixture and the resulting mixture was stirred until the loratadine was completely dissolved. The mixture was cooled to room temperature. The formulations prepared are summarized in Table 1 below:

TABLE 1

Loratadine Formulations with Mono-diglyceride of Medium Chain Fatty Acid Solvent System

| Ingredient | Formula 4-1 (mg/capsule) (% w/w) | Formula 4-2 (mg/capsule) (% w/w) | Formula 4-3 (mg/capsule) (% w/w) |
|---|---|---|---|
| Capmul™ MCM-C8 | 139 mg (86.9%) | 201.5 mg (88.2%) | 264 mg (89.2%) |
| Povidone | 10 mg (6.3%) | 15 mg (6.6%) | 20 mg (6.8%) |
| Polysorbate™ 80 | 1 mg (0.8%) | 1.5 mg (0.7%) | 2 mg (0.7%) |
| Loratadine | 10 mg (6.3%) | 10 mg (4.4%) | 10 mg (3.4%) |
| Fill weight | 160 mg (100.0%) | 228 mg (100.0%) | 296 mg (100.0%) |
| Fill volume (minim) | 2.60 minim | 3.70 minim | 4.80 minim |

Density = 1.0 g/ml

EXAMPLE 2

Preparation of Comparative Loratadine Formulations

In a manner similar to that of Example 1, the following formulations were prepared in accordance with the corresponding ingredients and proportions:

TABLE 2

Loratadine Formulations with PEG (Macrogol™ 400)/Propylene Glycol Solvent System

| Ingredient | Formula 1-1 (mg/capsule) (% w/w) | Formula 1-2 (mg/capsule) (% w/w) | Formula 1-3 (mg/capsule) (% w/w) | Formula 1-4 (mg/capsule) (% w/w) |
|---|---|---|---|---|
| PEG 400 (Macrogol™ 400) | 260 mg (87.8%) | 305 mg (88.4%) | 360 mg (88.7%) | 408 mg (88.9%) |
| Propylene Glycol | 26 mg (8.8%) | 30 mg (8.7%) | 36 mg (8.9%) | 41 mg (8.9%) |
| Loratadine | 10 mg (3.4%) | 10 mg (2.9%) | 10 mg (2.5%) | 10 mg (2.2%) |
| Fill weight | 296 mg (100.0%) | 345 mg (100.0%) | 406 mg (100.0%) | 459 mg (100.0%) |
| Capsule size (minim) | 5 minim oval | 6 minim oval | 7.5 minim oval | 8.5 minim oval |

Density = 1.08 g/ml

TABLE 3

Loratadine Formulations with PEG (Macrogol™ 400)/Propylene Glycol/Povidone Solvent System

| Ingredient | Formula 2-1 (mg/capsule) (% w/w) | Formula 2-2 (mg/capsule) (% w/w) | Formular 2-3 (mg/capsule) (% w/w) | Formula 2-4 (mg/capsule) (% w/w) |
|---|---|---|---|---|
| PEG 400 (Macrogol™ 400 | 260 mg (81.8%) | 285 mg (82.6%) | 336 mg (82.8%) | 381 mg (83.0%) |
| Propylene Glycol | 26 mg (8.2%) | 28 mg (8.1%) | 34 mg (8.4%) | 38 mg (8.3%) |
| Povidone | 22 mg (6.9%) | 22 mg (6.4%) | 26 mg (6.4%) | 30 mg (6.5%) |
| Loratadine | 10 mg (3.1%) | 10 mg (2.9%) | 10 mg (2.5%) | 10 mg (2.2%) |
| Fill weight | 318 mg (100.0%) | 345 mg (100.0%) | 406 mg (100.0%) | 459 mg (100.0%) |
| Capsule size (minim) | 5 minim oval | 6 minim oval | 7.5 minim oval | 8.5 minim oval |

Density = 1.1 g/ml

TABLE 4

Loratadine Formulations with PEG (Macrogol™ 400)/Propylene
Glycol/Polyoxyethylene 20 sorbitan monooleate (Polysorbate 80) Solvent System

| Ingredient | Formula 3A-1 (mg/capsule) (% w/w) | Formula 3A-2 (mg/capsule) (% w/w) | Formula 3B-1 (mg/capsule) (% w/w) | Formula 3B-2 (mg/capsule) (% w/w) |
|---|---|---|---|---|
| PEG 400 (Macrogol™ 400) | 89 mg (36.2%) | 108 mg (36.5%) | 96 mg (39.0%) | 116 mg (39.2%) |
| Propylene Glycol | 13 mg (5.3%) | 16 mg (5.4%) | 13 mg (5.3%) | 15 mg (5.1%) |
| Polysorbate™ 80 | 134 mg (54.5%) | 162 mg (54.7%) | 127 mg (51.6%) | 155 mg (52.4%) |
| Loratadine | 10 mg (4.1%) | 10 mg (3.4%) | 10 mg (4.1%) | 10 mg (3.4%) |
| Fill weight | 246 mg (100.0%) | 296 mg (100.0%) | 246 mg (100.0%) | 296 mg (100.0%) |
| Capsule size (minim) | 4 minim oval | 5 minim oval | 4 minim oval | 5 minim oval |

EXAMPLE 3

Comparative Storage Stability Study of Loratadine Compositions

The storage stability test was conducted on each of the above formulations by subjecting samples of each formulation to varying conditions. Each sample was prepared by either filling 3DXHB gel pouches with the formulation or a screw-capped brown glass bottle. Some of the samples were tested using pouches that were unsealed, and some of the samples tested were sealed using fresh gel. Each pouch sample was subjected to the following conditions: 1) 22° C. under ambient humidity, 2) 30° C. under 75% relative humidity (corresponding to accelerated solution stability test conditions), and 3) 5° C. under ambient humidity.

TABLE 5

Storage Stability at 5° C./Ambient Humidity of Loratadine
Formulation with PEG 400/Propylene Glycol Solvent System

| Formulation: | Container: | Storage Period: | Result: |
|---|---|---|---|
| 1-1 | Capped vial | 8 months | Clear/no crystals |
| 1-1 | Open gel pouch | 8 months | Crystallization |

As can be seen from the data in the above Table, no observable crystallization occurred in the conventional Macrogol™ 400 formulation in the capped vials at 5° C. and ambient humidity conditions. On the other hand, the Macrogol™ 400 formulation crystallized when stored in the open gel pouch. The results demonstrate that exposure of loratadine formulations to ambient moisture causes crystallization over time.

TABLE 6

Storage Stability at
22° C./Ambient Humidity of Loratadine Fill Formulations

| Formulation: | Container: | Storage Period: | Result: |
|---|---|---|---|
| ALL | Capped vial | 80 days | Clear/no crystals |
| 1-1 | Capped vial | 8 months | Clear/no crystals |

As can be seen in the above Table, none of the formulations tested had observable crystallization during a storage period of 80 days when contained in the capped vial at 22° C. and ambient humidity conditions.

TABLE 7

Storage Stability at 30° C./75% Relative Humidity of Loratadine
Formulation with PEG 400/Propylene Glycol Solvent System

| | Formula: | | | |
|---|---|---|---|---|
| | 1-1 | 1-2 | 1-3 | 1-4 |
| Days until crystallization (sealed gel pouch) | 8 days | 13 days | 13 days | 16 days |
| Days until crystallization (open gel pouch) | 5 days | 10 days | Not tested | Not tested |

As can be seen from the above data, storage at 30° C. and 75% relative humidity resulted in observable crystallization of the conventional loratadine formulations in the Macrogol™ 400 solvent system, and crystallization occurred in both sealed and open gel pouch containment. In the case of Formulas 1-1 and 1-2, crystallization occurred more rapidly in the open gel pouch than the sealed gel pouch.

TABLE 8

Storage Stability at 30° C./75% Relative Humidity of Loratadine
Formulation with PEG 400/Propylene Glycol/Povidone Solvent System

| | Formula: | | | |
|---|---|---|---|---|
| | 2-1 | 2-2 | 2-3 | 2-4 |
| Days until crystallization (sealed gel pouch) | 8 days | 10 days | 13 days | 15 days |
| Days until crystallization (open gel pouch) | 5 days | 10 days | Not tested | Not tested |

As the data shows, storage conditions of 30° C. and 75% relative humidity of loratadine formulations with a solvent system of Macrogol™ 400 in combination with povidone did not prevent crystallization from occurring in either sealed or open gel pouches.

TABLE 9

Storage Stability at 30° C./75% Relative Humidity of Loratadine Formulation with PEG 400/Propylene Glycol/Polysorbate 80 Solvent System

| | Formula: | | | |
|---|---|---|---|---|
| | 3A-1 | 3A-2 | 3B-1 | 3B-2 |
| Days until crystallization (sealed gel pouch) | 16 days | 29 days | 19 days | 29 days |

The above data shows that loratadine formulations in a Macrogol™ 400 solvent system and Polysorbate™ 80 did not prevent crystallization under 30° C. and 75% relative humidity storage conditions.

TABLE 10

Storage Stability at 30° C./75% Relative Humidity of Loratadine Formulations with Mono-, Diglyceride of Medium Chain Fatty Acid Solvent Systems

| | Formula: | | |
|---|---|---|---|
| | 4-1 | 4-2 | 4-3 |
| Days until crystallization (sealed gel pouch) | No crystals after 1 year and 4 months | No crystals after 71 days | No crystals after 71 days |
| Days until crystallization (open gel pouch) | Not tested | No crystals after 73 days | No crystals after 92 days |

As can be seen from the above data, loratadine formulations prepared in accordance with Formula 4-1 of the invention as described above exhibited no observable crystallization even after 71 days in storage at 30° C. with 75% relative humidity conditions in either the open or sealed gel pouch containment. Further yet, no observable crystals were present in Formulation 4-1 of the invention even after 16 months in the sealed gel pouch containment.

EXAMPLE 4

Preparation of Dosage Form Comprising Loratadine and Carrageenan Capsule Material In a process similar to that set forth in Example 1, the following fill formulation containing loratadine as an active ingredient was prepared:

TABLE 11

Loratadine Fill Formulation

| Ingredient | Formula 5 (mg/capsule) (% w/w) |
|---|---|
| Capmul ™ MCM-C8 | 262.1 mg (89.5%) |
| Povidone | 19 mg (6.5%) |
| Polysorbate ™ 80 | 1.9 mg (0.6%) |
| Loratadine | 10 mg (3.4%) |
| Fill weight | 293.0 mg (100.0%) |

Density = 1.0 g/ml

A capsule material was prepared having the following composition:

TABLE 12

Carrageenan Capsule Material

| Ingredient | Amount (% w/w) |
|---|---|
| Purified Water | 8.0% |
| Disodium phosphate anhydrous | 1.3% |
| Hydroxypropyl starch | 43.2% |
| Carrageenan | 14.0% |
| Glycerin | 33.5% |
| Total: | 100.00% |

Carragenan (iota-form) was Satiagel USC2 obtained from Degussa Texturant Systems, Balogne, Billancou, France; and the hydroxypropyl starch was Pure-Cote B790 obtained from Grain Processing Corp., IA. Iota-carragenan, hydroxypropyl starch and anhydrous disodium phosphate were dispersed in the liquids and molted. The obtained molten mass was cast into ribbon in the conventional manner known to those skilled in the art. The fill formulation of Table 11 was encapsulated in the material of Table 12. The shell mass was pumped into an encapsulation apparatus where the capsules are formed by the rotary die process under controlled temperature and humidity conditions.

The resulting soft capsule dosage form was a 5 minim oval capsule containing 10 mg of loratadine as the active ingredient.

INDUSTRIAL APPLICABILITY

The loratadine compositions of the invention provide for the use of loratadine in soft capsule dosage forms such as soft gelatin capsules by improving its solubility under storage conditions without adversely affecting its bioavailability. The compositions of the invention offer the additional benefit of increasing the concentration of solubilized loratadine per total fill volume, which permits smaller fill volumes to be used to deliver the same dosage of the drug. Accordingly, smaller capsule sizes can be used to administer the drug to patients, thereby increasing patient comfort and reducing manufacturing costs.

The complete disclosures of all patents, patent applications and publications are incorporated herein by reference as if each were individually incorporated by reference. The invention has been described with reference to various specific and preferred embodiments and techniques. However, it should be understood that many variations and modifications can be made while remaining within the spirit and scope of the invention.

What is claimed is:

1. A soft capsule dosage form comprising a fill composition consisting essentially of:
    a) a decarbalkoxylated loratadine derivative in a pharmaceutically effective amount;
    b) a mixture of mono- and diglycerides of medium chain fatty acids;
    c) povidone;
    d) polyoxyethylene sorbitan fatty acid ester; and
    wherein said soft capsule has a capsule size of 5 minim or less to about 1 minim; and
    wherein the soft capsule comprises a capsule material comprising carrageenan.

2. The soft capsule dosage form according to claim 1 wherein the decarbalkoxylated loratadine derivative is descarboethoxyloratadine.

3. The soft capsule dosage form according to claim 1, wherein said carrageenan is iota-carrageenan.

4. The soft capsule dosage form according to claim 3, wherein the capsule material further comprises hydroxypropyl starch.

5. The soft capsule dosage form according to claim 4, wherein the capsule material further comprises glycerin.

6. The fast capsule dosage form according to claim 1, wherein the capsule material comprises the following formulation:

a) iota-carrageenan;
b) hydroxypropyl starch;
c) glycerin;
d) anhydrous disodium phosphate; and
e) water.

7. The soft capsule dosage form according to claim 6, wherein the capsule material further comprises an additive selected from the group consisting of flavoring agents, opacifying agents, preservatives, embrittlement inhibiting agents, colorants, dyes and pigments, and disintegrants.

* * * * *